US007723018B2

(12) United States Patent
Booher et al.

(10) Patent No.: US 7,723,018 B2
(45) Date of Patent: May 25, 2010

(54) METHODS OF ASSAYING FOR CELL CYCLE MODULATORS USING COMPONENTS OF THE UBIQUITIN LIGATION CASCADE

(75) Inventors: Robert Booher, San Francisco, CA (US); Esteban Masuda, Menlo Park, CA (US); Valeria Ossovskaya, San Francisco, CA (US); Brian Wong, San Mateo, CA (US)

(73) Assignee: Rigel Pharmaceuticals, Incorporated, South San Francisco, CA (US)

( * ) Notice: Subject to any disclaimer, the term of this patent is extended or adjusted under 35 U.S.C. 154(b) by 779 days.

(21) Appl. No.: 10/651,389

(22) Filed: Aug. 28, 2003

(65) Prior Publication Data

US 2004/0180353 A1 Sep. 16, 2004

Related U.S. Application Data

(60) Provisional application No. 60/407,487, filed on Aug. 30, 2002, provisional application No. 60/435,427, filed on Dec. 20, 2002.

(51) Int. Cl.
*C12Q 1/00* (2006.01)
*C12Q 1/68* (2006.01)
*G01N 33/53* (2006.01)
*G01N 33/567* (2006.01)

(52) U.S. Cl. .................................. 435/4; 435/6; 435/7.1; 435/7.21

(58) Field of Classification Search ....................... 435/4
See application file for complete search history.

(56) References Cited

U.S. PATENT DOCUMENTS

| 5,726,025 | A | 3/1998 | Kirschner et al. |
| 5,968,761 | A | 10/1999 | Rolfe et al. |
| 5,976,849 | A | 11/1999 | Hustad et al. |
| 6,060,262 | A | 5/2000 | Beer-Romero et al. |
| 6,068,982 | A | 5/2000 | Rolfe et al. |
| 2002/0025569 | A1 | 2/2002 | Caligiuri et al. |
| 2003/0105000 | A1* | 6/2003 | Pero et al. ............... 514/12 |

FOREIGN PATENT DOCUMENTS

| EP | 1487973 A0 | 12/2004 |
| WO | WO 01/75145 A2 | 10/2001 |
| WO | WO 02/06485 A2 | 1/2002 |
| WO | WO 02/48324 A1 | 6/2002 |
| WO | WO 2004/020458 A2 | 3/2004 |

OTHER PUBLICATIONS

Fang and Weismann (Cellular and Molecular Life Sciences, 2004 61: 1546-1561).*
Pei and Tuschl (Nature Methods, 2006, 3: 670-676).*
Allen et al (TIBS, 1995 20:511).*
Sanchez and Dynlacht (Seminars in Cell & Developmental Biology, 2005, 16:311-321).*
Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Scott et al (Nature Genetics, 1999, 21:440-443).*
Bork (Genome Research, 2000,10:398-400).*
Fields and Sternglanz (TIG, 1994, 10:286-292).*
Liu et al. (J. Biol. Chem.1996, 271:2817-2822).*
Hirashima (Int. Arch. Allergy Immunol., 2000, Suppl 1:6-9).*
Benedict et al (J. Exp. Medicine, 2001,193(1)89-99).*
Jiang et al (J. Biol. Chem. 2003, 278(7) 4763-4769).*
Straub P et al. (J Biol. Chem. 1993 268(29): 21997-2003).*
Kouklis PD et al. (J Cell Science, 1993106(pt 3): 919-28).*
Honda et al. (FEBS Letters, 1997, 420:25-27).*
Desterro, Joana M.P. et al.; "Identification of the Enzyme Required for Activation of the Small Ubiquitin-like Protein SUMO-1"; 1999, *The Journal of Biological Chemistry*, vol. 274, No. 15, pp. 10618-10624.
Jentsch, Stefan et al.; "Ubiquitin and its kin: How close are the family ties?"; 2000, *Trends in Cell Biology*, vol. 10, pp. 335-342.
Wilkinson, Keith D.; "Ubiquitin-Dependent Signaling: The Role of Ubiquitination in the Response of Cells to Their Environment"; 1999, *J. Nutr.*, vol. 129, No. 11, pp. 1933-1936.
Ayusawa et al., "Complementation by a Cloned Human Ubiquitin-Activating Enzyme E1 of the S-Phase-Arrested Mouse FM3A Cell Mutant with Thermolabile E1," *Cell Structure and Function*, 17:113-122 (1992).
Banerjee et al., "Characterization of a Dominant Negative Mutant of the Cell Cycle Ubiquitin-conjugating Enzyme Cdc34," *Journal of Biological Chemistry*, 270(44):26209-26215 (1995).
Coux et al., "Enzymes Catalyzing Ubiquitination and Proteolytic Processing of the p105 Precursor of Nuclear Factor κB1," *Journal of Biological Chemistry*, 273(15):8820-8828 (1998).
Database EMBL [Online], "*Homo sapiens* OK/SW-cl.73 mRNA for ubiquitin carrier protein, complete cds.," Accession No. AB062397, XP-002383017, May 27, 2002.
Database Geneseq [Online]; "Human cancer associated protein sequence SEQ ID No. 979," Accession No. AAB43534, XP-002383018, Feb. 8, 2001.
Database Geneseq [Online]; "Human ubiquitin-conjugating enzyme E2," Accession No. AAB28191, XP-002383019, Jan. 30, 2001.
Database Geneseq [Online]; "Protein E2-EPF differentially expressed in breast cancer tissue," Accession No. AAU84331, XP-002383020, May 8, 2002.

(Continued)

*Primary Examiner*—Peter J Reddig
(74) *Attorney, Agent, or Firm*—James J. Diehl; Travis Young; Klarquist Sparkman, LLP

(57) ABSTRACT

The present invention relates to regulation of the cell cycle. More particularly, the present invention is directed to nucleic acids encoding components of the ubiquitin ligation pathway, e.g., ubiquitin and ubiquitin-like molecules, E1, E2, and E3 proteins and their substrates, which are involved in modulation of cell cycle arrest. The invention further relates to methods for identifying and using agents, including small molecule chemical compositions, antibodies, peptides, cyclic peptides, nucleic acids, RNAi, antisense nucleic acids, and ribozymes, that modulate cell cycle arrest via modulation of the ubiquitin ligation pathway; as well as to the use of expression profiles and compositions in diagnosis and therapy related to cell cycle regulation and modulation of cellular proliferation, e.g., for treatment of cancer and other diseases of cellular proliferation.

13 Claims, 6 Drawing Sheets

OTHER PUBLICATIONS

Database UniProt [Online], "Ubiquitin-conjugating enzyme E2S (EC 6.3.2.19) (Ubiquitin-conjugating enzyme E2-24 kDA) (Ubiquitin-protein ligase) (Ubiquitin carrier protein) (E2-EPF5)," Accession No. Q16763, XP-002383016, Nov. 1, 1997.

Fang et al., "Dysregulation of T lymphocyte function in itchy mice: a role for Itch in $T_H2$ differentiation," *Nature Immunology*, 3(3):281-287 (2002).

Handley et al., "Molecular cloning, sequence, and tissue distribution of the human ubiquitin-activating enzyme E1," *Proc. Natl. Acad. Sci. USA*, 88:258-262 (1991).

Karin et al., Phosphorylation Meets Ubiquitination: The Control of NF-κB Activity, *Annual Review of Immunology*, 18:621-663 (2000).

King et al., "How Proteolysis Drives the Cell Cycle," *Science*, 274:1652-1659 (1996).

Kwon et al., "Evidence for Involvement of the Proteasome Complex (26S) and NFκB in IL-1β-Induced Nitric Oxide and Prostaglandin Production by Rat Islets and RINm5F Cells," *Diabetes*, 47:583-591 (1998).

Liu et al., "cDNA Cloning of a Novel Human Ubiquitin Carrier Protein," *Journal of Biological Chemistry*, 267(22):15829-15835, (1992).

Meiners et al., "Ubiquitin-Proteasome Pathway as a New Target for the Prevention of Restenosis," *Circulation, American Heart Association*, 105(4):483-489 (2002).

Pagano, "Cell cycle regulation by the ubiquitin pathway," *FASEB Journal*, 11:1067-1075 (1997).

Perry et al., "The itchy locus encodes a novel ubiquitin protein ligase that is disrupted in $a^{18H}$ mice," *Nature Genetics*, 18:143-146 (1998).

Stephen et al., "The Ubiquitin-activating Enzyme E1 Is Phosphorylated and Localized to the Nucleus in a Cell Cycle-dependent Manner," *Journal of Biological Chemistry*, 271(26):15608-15614 (1996).

Swinney et al., "A Small Molecule Ubiquitination Inhibitor Blocks NF-κB-dependent Cytokine Expression in Cells and Rats," *Journal of Biological Chemistry*, 277(26):23573-23581 (2002).

Yaron et al., "Identification of the receptor component of the IκBα-ubiquitin ligase," *Nature*, 396:590-594 (1998).

Zacksenhaus et al., "Molecular cloning, primary structure and expression of the human X linked A1S9 gene cDNA which complements the ts A1S9 mouse L cell defect in DNA replication," *The EMBO Journal*, 9(9):2923-2929 (1990).

Zhang et al., "The SOCS box of suppressor of cytokine signaling-1 is important for inhibition of cytokine action in vivo," *PNAS*, 98(23):13261-13265 (2001).

D'Andrea & Serhan, "Relieving the Itch" *Nature Genetics* 18:97-99 (1998).

\* cited by examiner

Figure 1

E1: ubiquitin activating enzyme

| E1 | Alias | ORF | Prot | Modifier | siRNA induced cell cycle arrest | Notes |
|---|---|---|---|---|---|---|
| E1 | UBA1, UBE1, A1S9 | NM_003334 | NP_003325 | Ub | G1 and G2/M; apoptosis | |
| MOP-4 | MOP-4 | AB014773 | BAB19785 | FAT10 | G2/M; apoptosis | |
| FLJ14657 | | NM_024818 | NP_079094 | unknown | NE | |
| UBA3 | UBE1C, yeast UBA3 homolog | NM_003968 | NP_003959 | Nedd8 | G2/M; apoptosis | |
| UBA3, 1 mismatch | UBA3 | AF046024 | AAC27648 | Nedd8 | ND | Shorter version |
| UBA2 | UBA2, SAE2 | NM_005499 | NP_005490 | SUMO | NE | |
| SAE1 | AOS1, HSPC140, SUA1 | NM_005500 | NP_005491 | SUMO | G1; G2/M | UBA2 partner |
| SAE1 isoform | AOS1, LOC160202 | XM_090110 | XP_090110 | SUMO | G1 | UBA2 partner |
| UBE1L | UBE1L, UAE2 | NM_003335 | NP_003326 | ISG-15 | G1; G2/M | |
| hAPG7 | hGSA7, hAPG7. | NM_006395 | NP_006386 | Apg8, Apg12 | NE | |
| hAPG7 isoform | MGC:1334 IMAGE:3504204 | BC000091 | AAH00091 | Apg8, Apg12 | G2/M, apoptosis | |
| APPBP1 | APPBP1 | NM_003905 | NP_003896 | Nedd8 | NE | UBA3 partner |
| MOCS3, molybdopterin synthase sulfurylase | MGC:9252 IMAGE:3908290 | NM_014484 | NP_055299 | | NE | |
| MOCS3 short | | | | | G2/M | 39aa exon deletion |

Figure 2

E2: ubiquitin conjugating enzyme

| E2 | Alias | ORF | Prot | Previously identified function (Mammals Only) | Modifier | siRNA induced cell cycle arrest | HeLa DN GFP/Cell Tracker | A549 DN GFP/CT |
|---|---|---|---|---|---|---|---|---|
| UBE2D1 Hs UBC4/5 homolog | UBE2D1, UBCH5A, UBC4/5 homolog | NM_003338.1 | NP_003329.1 | Mediates E6-AP ubiquitylation of p53 | Ub | | NE | |
| UBC9 Hs | UBC9, UBE2I | NM_003345.1 | NP_003336.1 | Multiple - Localization | SUMO | | NE | |
| FTS homolog Hs +1aa | fused toes homolog, FLJ13258 | NM_022476.1 | NP_071921.1 | Apoptosis, Limb and Thymic Development | unknown | G2/M, apoptosis | NE | |
| MGC:13396 Hs | MGC:13396, IMAGE:4081461 | BC010900.1 | AAH10900.1 | unknown | unknown | | NE | |
| UBE2V2 Hs | UBE2V2, EDAF-1, MMS2, UEV2, DDVIT1, EDPF1 | NM_003350.2 | NP_003341.1 | unknown | Lacks catalytic cys, K63 Ub | | NE | |
| MGC:10481 Hs | MGC:10481, IMAGE:3838157 | BC004862.1 | AAH04862.1 | unknown | unknown | G2/M | NE | |
| XM_054332.1 Hs | | XM_054332.1 | XP_054332.1 | unknown | unknown | | NE | |
| FLJ13855 Hs | FLJ13855 | XM_030444.3 | XP_030444.1 | unknown | unknown | G2/M | NE | |
| E2-230K homolog Hs | E2-230K ortholog, FLJ12878, | NM_022066.1 | NP_071349.1 | unknown | unknown | NE | | |

Fig. 2 cont'd

| E2 | Alias | ORF | Prot | Previously identified function (Mammals Only) | Modifier | siRNA induced cell cycle arrest | HeLa DN GFP/Cell Tracker | A549 DN GFP/CT |
|---|---|---|---|---|---|---|---|---|
| UBE2V2 Hs | KIAA1734 | | | | | | | |
| | UBE2D2, UBCH5B, UBC4, UBC4/5 homolog | NM_003339.1 | NP_003330.1 | Mediates E6-AP ubiquitylation of p53 | Ub | | NE | |
| UBE2D3 Hs 1 SNP | UBE2D3, UBCH5C, UBC4/5 homolog | NM_003340.1 | NP_003331.1 | cdc34 | Ub | NE | NE | |
| Non-canon Ub-conj Enz (NCUBE1) Hs | NCUBE1, HSU93243, HSPC153, CGI-76 | NM_016336.2 | NP_057420.2 | ER-associated Degradation | Ub | | NE | |
| HSPC150 Hs | | NM_014176.1 | NP_054895.1 | unknown | unknown | | NE | |
| UBC8 Hs | UBE2H, UBCH, UBCH2, UBC8 homolog | NM_003344.1 | NP_003335.1 | unknown | Ub | G2/M | NE | |
| UBC8 Hs 6SNP | UBE2H, UBCH, UBCH2, UBC8 homolog | NM_003344.1 | NP_003335.1 | | | | NE | |
| UBE2L3 Hs 2 SNP | UBE2L3, UBCH7 | NM_003347.1 | NP_003338.1 | p53 degradation | Ub | | INH | |
| UBE2E1 Hs | UBE2E1, UBCH6, UBC4/5 homolog | NM_003341.1 | NP_003332.1 | unknown | Ub | NE | | |

Fig. 2 cont'd

| E2 | Alias | ORF | Prot | Previously identified function (Mammals Only) | Modifier | siRNA induced cell cycle arrest | HeLa DN GFP/Cell Tracker | A549 DN GFP/CT |
|---|---|---|---|---|---|---|---|---|
| RAD6/UBE2A Hs | UBE2A, RAD6A, HHR6A, UBC2, RAD6 homolog | NM_003336.1 | NP_003327.1 | spermatogenesis (-/-), DNA Repair | Ub | NE | NE | |
| UBE2E3 Hs | UBE2E3, UBCH9, UBC4/5 homolog | NM_006357.1 | NP_006348.1 | unknown | Ub | G2/M | NE | |
| UBC12/UBE2M Hs | UBE2M, HUBC12, UBC12 homolog | NM_003969.1 | NP_003960.1 | Regulation of SCF complex/cell cycle/NF-kB | NEDD8 | G2/M | NE | |
| UBC6 Hs | UBC6 | AF296658.1 | AAK52609.1 | ERAD | Ub | G2/M | 374%/1.4 | 38%/1.3 |
| NEDD8-conj enzyme 2 (NCE2) Hs | NCE2 | NM_080678.1 | NP_542409.1 | unknown | NEDD8 | ND | | |
| CDC34 Hs | CDC34, E2-CDC34, E2-32 complementing | NM_004359.1 | NP_004350.1 | Transcription regulation, G1-S | Ub | | NE | 6%/0.8 |
| UBC13/UBE2N Hs | UBE2N, UBCH-BEN, UBC13 hom., sim to bendless | NM_003348.1 | NP_003339.1 | IKK/NF-kB activation | unknown | NE | | |

Figure 3
E3: ubiquitin ligase

| E3 | Orf | Prot | siRNA induced cell cycle arrest |
|---|---|---|---|
| APC11 | NM_016476 | NP_057560 | G2 |
| APC2 | NM_013366 | NP_037498 | G2 |
| Roc1 | NM_014248 | NP_055063 | S, G2 |

Figure 4
Ubiquitin-like molecule

| Ubl | Alias | ORF | Prot |
|---|---|---|---|
| Ubiquitin | | NM_002954.2 | NP_002945 |
| NEDD-8 | | NM_006156.1 | NP_006147 |
| ISG-15 | UCRP | NM_005101.1 | NP_005092.1 |
| APG12 | APG12L,MAP1_LC3 | NM_004707.1 | NP_004698.1 |
| APG8 | MAP1_LC3, MAP1A, 1BLC3 | NM_022818.2 | NP_073729.1 |
| Fat10 | Diubiquitin | NM_006398.1 | NP_006389.1 |
| Fau, Fubi | FBR-MuSV-associated ubiquitously expressed gene,ubiquitin-like protein fubi,40S ribosomal protein S30,FAU-encoded ubiquitin-like protein | NM_001997.2 | NP_001988.1 |
| SUMO-1 | Sentrin1,SMT3C,GMP1,PIC,SM,SMT3H3 | NM_003352.2 | NP_003343.1 |
| SUMO-2 | Sentrin3,SMT3A,SMT3H1 | NM_006936.1 | NP_008867.1 |
| SUMO-3 | SMT3B,SMT3H2,HSMT3 | NM_006937.2 | NP_008868.2 |

SEQUENCE LISTING

<160> NUMBER OF SEQ ID NOS: 2

<210> SEQ ID NO 1
<211> LENGTH: 881
<212> TYPE: DNA
<213> ORGANISM: homo sapiens
<300> PUBLICATION INFORMATION:
<308> DATABASE ACCESSION NUMBER: XM_054332
<309> DATABASE ENTRY DATE: 2001-08-27
<313> RELEVANT RESIDUES IN SEQ ID NO: (1)..(881)

<400> SEQUENCE: 1

```
ggcggaccga agaacgcagg aaggggggccg gggggacccg ccccggccg gccgcagcca      60
tgaactccaa cgtggagaac ctaccccgc acatcatccg cctggtgtac aaggaggtga     120
cgacactgac cgcagaccca cccgatggca tcaaggtctt cccaacgag gaggacctca     180
ccgacctcca ggtcaccatc gagggccctg agggggacccc atatgctgga ggtctgttcc     240
gcatgaaact cctgctgggg aaggacttcc ctgcctcccc acccaagggc tacttcctga     300
ccaagatctt ccacccgaac gtgggcgcca atggcgagat ctgcgtcaac gtgctcaaga     360
gggactggac ggctgagctg ggcatccgac acgtactgct gaccatcaag tgcctgctga     420
tccacccctaa ccccgagtct gcactcaacg aggaggcggg ccgcctgctc ttggagaact     480
acgaggagta tgcggctcgg gcccgtctgc tcacagagat ccacggggc gccggcgggc     540
ccagcggcag ggccgaagcc ggtcgggccc tggccagtgg cactgaagct tcctccaccg     600
accctggggc cccagggggc ccgggagggg ctgagggtcc catggccaag aagcatgctg     660
gcgagcgcga taagaagctg gcggccaaga aaaagacgga caagaagcgg gcgctgcggc     720
ggctgtagtg ggctctcttc ctccttccac cgtgacccca acctctcctg tcccctccct     780
ccaactctgt ctctaagtta tttaaattat ggctggggtc ggggagggta caggggggcac     840
tgggacctgg atttgttttt ctaaataaag ttggaaaagc a                        881
```

<210> SEQ ID NO 2
<211> LENGTH: 222
<212> TYPE: PRT
<213> ORGANISM: homo sapiens
<300> PUBLICATION INFORMATION:
<308> DATABASE ACCESSION NUMBER: XP_054332
<309> DATABASE ENTRY DATE: 2001-08-27
<313> RELEVANT RESIDUES IN SEQ ID NO: (1)..(222)

<400> SEQUENCE: 2

```
Met Asn Ser Asn Val Glu Asn Leu Pro Pro His Ile Ile Arg Leu Val
1               5                   10                  15

Tyr Lys Glu Val Thr Thr Leu Thr Ala Asp Pro Pro Asp Gly Ile Lys
            20                  25                  30

Val Phe Pro Asn Glu Glu Asp Leu Thr Asp Leu Gln Val Thr Ile Glu
        35                  40                  45

Gly Pro Glu Gly Thr Pro Tyr Ala Gly Gly Leu Phe Arg Met Lys Leu
    50                  55                  60

Leu Leu Gly Lys Asp Phe Pro Ala Ser Pro Pro Lys Gly Tyr Phe Leu
65                  70                  75                  80

Thr Lys Ile Phe His Pro Asn Val Gly Ala Asn Gly Glu Ile Cys Val
                85                  90                  95

Asn Val Leu Lys Arg Asp Trp Thr Ala Glu Leu Gly Ile Arg His Val
            100                 105                 110
```

-continued

```
Leu Leu Thr Ile Lys Cys Leu Leu Ile His Pro Asn Pro Glu Ser Ala
        115                 120                 125

Leu Asn Glu Glu Ala Gly Arg Leu Leu Leu Glu Asn Tyr Glu Glu Tyr
    130                 135                 140

Ala Ala Arg Ala Arg Leu Leu Thr Glu Ile His Gly Gly Ala Gly Gly
145                 150                 155                 160

Pro Ser Gly Arg Ala Glu Ala Gly Arg Ala Leu Ala Ser Gly Thr Glu
                165                 170                 175

Ala Ser Ser Thr Asp Pro Gly Ala Pro Gly Gly Pro Gly Gly Ala Glu
            180                 185                 190

Gly Pro Met Ala Lys Lys His Ala Gly Glu Arg Asp Lys Lys Leu Ala
        195                 200                 205

Ala Lys Lys Lys Thr Asp Lys Lys Arg Ala Leu Arg Arg Leu
    210                 215                 220
```

METHODS OF ASSAYING FOR CELL CYCLE MODULATORS USING COMPONENTS OF THE UBIQUITIN LIGATION CASCADE

CROSS-REFERENCES TO RELATED APPLICATIONS

The present application claims the benefit of U.S. Ser. No. 60/407,487, filed Aug. 30, 2002, and U.S. Ser. No. 60/435,427, filed Dec. 20, 2002, each herein incorporated by reference in their entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of the cell cycle. More particularly, the present invention is directed to nucleic acids encoding components of the ubiquitin ligation pathway, e.g., ubiquitin and ubiquitin-like molecules, E1, E2, and E3 proteins and their substrates, which are involved in modulation of cell cycle arrest. The invention further relates to methods for identifying and using agents, including small molecule chemical compositions, antibodies, peptides, cyclic peptides, nucleic acids, RNAi, antisense nucleic acids, and ribozymes, that modulate cell cycle arrest via modulation of the ubiquitin ligation pathway; as well as to the use of expression profiles and compositions in diagnosis and therapy related to cell cycle regulation and modulation of cellular proliferation, e.g., for treatment of cancer and other diseases of cellular proliferation.

BACKGROUND OF THE INVENTION

Cell cycle regulation plays a critical role in neoplastic disease, as well as disease caused by non-cancerous, pathologically proliferating cells. Normal cell proliferation and progress through the phases of the cell cycle ($G_1$, S, $G_2$, and M, also the $G_0$ state) is tightly regulated by the activation and deactivation of a series of proteins that constitute the cell cycle machinery. The expression and activity of components of the cell cycle can be altered during the development of a variety of human disease such as cancer, cardiovascular disease, psoriasis, where aberrant proliferation contributes to the pathology of the illness. There are genetic screens to isolate important components for cell cycle regulation using different organisms such as yeast, worms, flies, etc. However, involvement of a protein in cell cycle regulation in a model system is not always indicative of its role in cancer and other proliferative disease. Thus, there is a need to establish screening for understanding human diseases caused by disruption of cell cycle regulation. Identifying proteins, their ligands and substrates, and downstream signal transduction pathways involved in cell cycle regulation and neoplasia in humans is important for developing therapeutic regents to treat cancer and other proliferative diseases.

BRIEF SUMMARY OF THE INVENTION

The present invention therefore provides nucleic acids encoding protein components of the ubiquitin ligation cascade such as ubiquitin and ubiquitin-like molecules, E1, E2, and E3, and their substrates, which are involved in cell cycle modulation. The invention provides methods of screening for compounds, e.g., small organic molecules, antibodies, peptides, cyclic peptides, nucleic acids, antisense molecules, RNAi, and ribozymes, that are capable of modulating cellular proliferation and/or cell cycle regulation, e.g., inhibiting cellular proliferation, or activating apoptosis. Therapeutic and diagnostic methods and reagents are also provided. Modulators of the ubiquitin ligase cascade are therefore useful in treatment of cancer and other proliferative diseases. The compounds of the invention are also useful for enhancing sensitivity of a cell to chemotherapeutic agents such as bleomycin and etoposide, and/or to reducing toxicity of chemotherapeutic agents.

In one aspect, the present invention provides a method for identifying a compound that modulates the cell cycle, the method comprising the steps of: (i) contacting a cell comprising a polypeptide from FIG. 1, column 1, FIG. 2, column 1, or FIG. 3, column 1, or a fragment thereof, with the compound, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3; and (ii) determining the effect of the compound upon the cell comprising the polypeptide or fragment thereof, thereby identifying a compound that modulates the cell cycle.

In one embodiment, modulation of the cell cycle is associated with cancer. In another embodiment, modulation of the cell cycle causes cellular proliferation. In another embodiment, modulation of the cell cycle causes apoptosis. In another embodiment, modulation of the cell cycle causes cell cycle arrest.

In one embodiment, the effect of the compound on the cell is determined by measuring cell cycle arrest, lymphocyte proliferation, cancer cell proliferation, or apoptosis. In another embodiment, the effect of the compound on the cell is determined by cell tracker dye assay and FACS analysis. In another embodiment, the effect of the compound on the cell is determined by BRDU staining assay and FACS analysis. In another embodiment, the cell cycle modulation is measured by assaying DNA synthesis, DNA content, or fluorescent marker level. In another embodiment, DNA synthesis or content is measured by 3H thymidine incorporation, BrdU incorporation, or Hoescht staining.

In another embodiment, the fluorescent marker is selected from the group consisting of a cell tracker dye or green fluorescent protein.

In one embodiment, modulation is activation of cell cycle arrest. In another embodiment, modulation is activation of cancer cell cycle arrest.

In one embodiment, the host cell is a lymphocyte. In another embodiment, the host cell is a cancer cell. In another embodiment, the cancer cell is a breast, prostate, colon, or lung cancer cell. In another embodiment, the cancer cell is a transformed cell line. In another embodiment, the transformed cell line is PC3, H1299, MDA-MB-231, MCF7, A549, or HeLa. In another embodiment, the cancer cell is p53 null or mutant. In another embodiment, the cancer cell is p53 wild-type.

In one embodiment, the polypeptide is recombinant. In another embodiment, the polypeptide is encoded by a nucleic acid comprising a sequence selected from FIG. 1, column 3, FIG. 2, column 3, or FIG. 3, column 3.

In one embodiment, the compound is an RNAi molecule, antibody, antisense molecule, small organic molecule, or a peptide, e.g., circular peptide.

In one aspect, the present invention provides a method for identifying a compound that modulates the cell cycle, the method comprising the steps of: (i) contacting a polypeptide from FIG. 1, column 1, FIG. 2, column 1, or FIG. 3, column 1, or a fragment thereof, with the compound, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3; (ii) determining the effect of the compound upon the polypeptide or fragment thereof; and (iii) contacting a cell comprising the polypeptide with the compound; and (iv) determining the effect of the compound upon a cell comprising the polypeptide or fragment thereof, thereby identifying a compound that modulates the cell cycle.

In another aspect, the present invention provides a method for identifying a compound that modulates the cell cycle, the method comprising the steps of: (i) contacting a polypeptide from FIG. 1, column 1, FIG. 2, column 1, or FIG. 3, column 1, or a fragment thereof, with the compound, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3; and (ii) determining the effect of the compound upon the polypeptide or fragment thereof in vitro using a ubiquitin ligase assay, thereby identifying a compound that modulates the cell cycle.

In another aspect, the present invention provides a method of identifying a cell cycle modulating compound, comprising: (i) combining (a) a ubiquitin activating agent (E1) selected from the E1s listed in FIG. 1, column 1, (b) a ubiquitin moiety or a ubiquitin-like moiety which binds with said E1 in the process of ubiquitin activation and (c) a compound, under conditions in which said E1 normally forms a bond with said ubiquitin moiety or ubiqiutin-like moiety and; (ii) determining the binding of said E1 and said ubiquitin moiety or ubiquitin like-moiety, wherein an alteration in binding between said E1 and said ubiquitin moiety or ubiqiutin like moiety as compared with binding in the absence of said compound indicates that said compound modulates the cell cycle.

In another aspect, the present invention provides a method of identifying a cell cycle modulating compound, comprising: (i) combining (a) a ubiquitin conjugating agent (E2) selected from the E2s listed in FIG. 2, column 1, (b) a ubiquitin activating agent (E1) capable of transferring an activated ubiquitin moiety to said E2, (c) a ubiquitin moiety or a ubiquitin like moiety capable of being activated by said E1 and subsequently binding said E2 and (d) a compound, under conditions in which said E1 normally transfers an activated ubiquitin moiety or ubiquitin like moiety to said E2 and; (ii) determining the binding of said E2 and said ubiquitin moiety or ubiquitin like moiety, wherein an alteration in binding between said E2 and said ubiquitin moiety or ubiquitin like moiety as compared with binding in the absence of said compound indicates that said compound modulates the cell cycle.

In another aspect, the present invention provides method of identifying a cell cycle modulating compound, comprising: (i) combining (a) a ubiquitin ligating agent (E3) selected from the E3s listed in FIG. 3, column 1, (b) a ubiquitin conjugating agent (E2) capable of transferring an activated ubiquitin moiety or a ubiquitin like moiety to said E3, (c) a ubiquitin activating agent (E1) capable of transferring an activated ubiquitin moiety or ubiquitin like moiety to said E2, (d) a ubiquitin moiety or a ubiquitin like moiety capable of being activated by said E1 and subsequently transferred, via said E2, and binding said E3 and (e) a compound, under conditions in which said E2 normally transfers an activated ubiquitin moiety or ubiquitin like moiety to said E3 and; (ii) determining the binding of said E3 and said ubiquitin moiety or ubiquitin like moiety, wherein an alteration in binding between said E3 and said ubiquitin moiety as compared with binding in the absence of said compound modulates the cell cycle.

In one embodiment, the E2 is SEQ ID NO: 2, which is the polypeptide encoded by XM_054332 (deposited with GenBank on Aug. 27, 2001), UbcH9, or Ubc112. In another embodiment, the E1 is SAL1 or UBE1L.

In another aspect, the present invention provides a method for identifying a compound that modulates the cell cycle, the method comprising the steps of: (i) contacting a cell comprising a polypeptide from FIG. 1, column 1, FIG. 2, column 1, or FIG. 3, column 1, or a fragment thereof, with the compound, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3; and (ii) determining the effect of the compound upon the cell comprising the polypeptide or fragment thereof using an assay comprising application of a dye selected from the group consisting of a cell tracker dye and BRDU, and FACS analysis of the cells, thereby identifying a compound that modulates the cell cycle.

In one embodiment, the E1 is SAL1 or UBE1L and the E2 is SEQ ID NO: 2, which is the polypeptide encoded by XM_054332 (deposited with GenBank on Aug. 27, 2001), UbcH9, or Ubc12.

In another aspect, the present invention provides a method of modulating the cell cycle of a cell comprising, (i) providing a cell comprising a polypeptide, or naturally occurring variant thereof, selected from: a peptide of FIG. 1, column 1, a peptide of FIG. 2, column 2; and a peptide of FIG. 3, column 3; and (ii) contacting said cell with an inhibitor of said polypeptide, whereby the cell cycle of said cell is modulated.

In another aspect, the present invention provides a method of modulating the cell cycle in a subject, the method comprising the step of administering to the subject a therapeutically effective amount of a compound identified using the method described herein.

In one embodiment, the modulation of the cell cycle is associated with cancer.

In one embodiment, the subject is a human. In another embodiment, the subject has cancer.

In another embodiment, the compound inhibits cancer cell proliferation.

In one aspect, the present invention provides a method of modulating the cell cycle in a subject, the method comprising the step of administering to the subject a therapeutically effective amount of a polypeptide from FIG. 1, column 1, FIG. 2, column 1, or FIG. 3, column 1, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3.

In another aspect, the present invention provides a method of modulating the cell cycle in a subject, the method comprising the step of administering to the subject a therapeutically effective amount of a nucleic acid encoding a polypeptide from FIG. 1, column 1, FIG. 2, column 1, or FIG. 3, column 1, the polypeptide encoded by a nucleic acid that hybridizes under stringent conditions to a nucleic acid encoding a polypeptide having an amino acid sequence as identified in FIG. 1, column 4, FIG. 2, column 4, or FIG. 3, column 3.

In another aspect, the present invention provides a method for identifying a compound capable of interfering with binding of a component of the ubiquitin ligation pathway or fragment thereof, the method comprising the steps of: (i) combining a first polypeptide of FIG. 1, column 1, with a second polypeptide of FIG. 2, column 1, or fragment thereof; and (ii) determining the binding of the first polypeptide or fragment thereof to the second polypeptide.

In another aspect, the present invention provides a method for identifying a compound capable of interfering with binding of a component of the ubiquitin ligation pathway or fragment thereof, the method comprising the steps of: (i) combining a first polypeptide of FIG. 1, column 1, with a second polypeptide of FIG. 4, column 1, or fragment thereof; and (ii) determining the binding of the first polypeptide or fragment thereof to the second polypeptide.

In one embodiment, the first polypeptide or fragment thereof and the second polypeptide are combined first. In another embodiment, the first polypeptide or fragment thereof and the second polypeptide are expressed in a cell. In another embodiment, the cell is a yeast cell or a mammalian cell. In another embodiment, the first polypeptide or fragment thereof is fused to a heterologous polypeptide. In another embodiment, the binding of the first polypeptide or fragment thereof to the second polypeptide is determined by measuring reporter gene expression.

In one aspect, the present invention provides methods of ubiquitinating a substrate in vitro or in vivo by providing a ubiquitin ligation cascade molecule. In another aspect, the present invention provides methods of modulating a protein by ubiquitination, e.g., by overexpression of a ubiquitin ligation cascade molecule or by modulation of a ubiquitin ligation cascade molecule.

In one aspect, the present invention provides a method of inducing cell cycle arrest of a cell, the method comprising the step of administering to the cell a vector expressing an siRNA molecule, wherein the siRNA molecule is from 21 to 30 nucleotide base pairs in length and wherein the siRNA molecule is specific for a nucleic acid encoding a polypeptide having an amino acid sequence as identified in FIG. 1, column 4, FIG. 2, column 4, or FIG. 3, column 3.

BRIEF DESCRIPTION OF THE DRAWINGS

FIG. 1 provides a list of E1 ubiquitin activating enzyme genes and the proteins encoded by the genes that are involved in cell cycle modulation. NE: no effect. INH: inhibition. ENH: enhanced. DN: dominant negative cDNA.

FIG. 2 provides a list of E2 ubiquitin conjugating enzyme genes and the proteins encoded by the genes that are involved in cell cycle modulation. NE: no effect. INH: inhibition. ENH: enhanced. DN: dominant negative cDNA.

FIG. 3 provides a list of E3 ubiquitin ligase genes and the proteins encoded by the genes that are involved in cell cycle modulation. NE: no effect. INH: inhibition. ENH: enhanced. DN: dominant negative cDNA.

FIG. 4 provides a list of ubiquitin moieties, including ubiquitin-like molecules (ubl), ubiquitin, and fragments thereof.

SEQUENCE LISTING

The nucleic and amino acid sequences listed in the accompanying sequence listing are shown using standard letter abbreviations for nucleotide bases, and three letter code for amino acids, as defined in 37 C.F.R. 1.1822.

SEQ ID NO: 1 is the nucleic acid sequence of XM_054332.

SEQ ID NO: 2 is the amino acid sequence of XP_054332.

DETAILED DESCRIPTION OF THE INVENTION

Introduction

The ubiquitin ligase cascade functions to regulate protein turnover in a cell by closely regulating the degradation of specific proteins. By regulating protein degradation, cells can quickly eliminate a protein that in turn regulates another function (e.g., a transcription factor that is needed to express a particular gene). Furthermore, this form of control is very effective, as the elimination of a particular protein ensures that the process governed by the protein is shut-down. In this process, ubiquitin or a ubiquitin-like protein (see FIG. 4) is covalently ligated to a target or substrate protein, resulting in a polyubiquitinated target protein that is rapidly detected a degraded by the 26S proteasome. E1 enzymes of the ubiquitin ligation cascade are known as "ubiquitin-activating enzymes." These enzymes activate ubiquitin in an ATP-dependent manner so that the ubiquitin is in a reactive state. E2 enzymes are known as "ubiquitin conjugating enzymes." These enzymes are involved in catalyzing the attachment of ubiquitin to the substrate protein. E3 enzymes are known as "ubiquitin ligases." E3s function in concert with E2 enzymes, sometimes in preferred pairs, and link the ubiquitin to the substrate molecule to form polyubiquitinated substrates. E3s are thought to play a role in recognizing the substrate protein. E3 molecules can have a single subunit responsible for the ligase activity, or can act as a multi-subunit complex. For a review of the ubiquitin ligation cascade and its components, see Weissman, *Nature Reviews* 2:169-178 (2001); Hans & Siepmann, *FASEB J.* 11:1257-1268 (1997). Identification of ubiquitin, ubiquitin-like molecules, E1, E2, and E3 enzymes is well known to those of skill in the art.

As described below, the present inventors for the first time have identified E1, E2, and E3 members of the ubiquitin ligase cascade as regulators of the cell cycle (see FIGS. 1, 2, and 3). These proteins were identified by functional knock-out studies, using, e.g., cDNA, peptide, and siRNA molecules. cDNA, peptide and siRNA molecules act, e.g., trans-dominant effectors (activator or inhibitor molecules such as peptides, siRNA, antisense molecules, ribozymes, antibodies, small organic molecules, etc.), or dominant negative mutants (e.g., cDNA encoding a dominant negative protein), and can be used in functional assays for cell cycle phenotype to validate members of the ubiquitin ligation cascade such as E1, E2, and E3 proteins as cell cycle modulators. It should be noted that some but not all effector molecules can produce an effect for any specific target. Therefore, a finding of "no effect" for a particular effector, such as a specific siRNA or cDNA, is not necessarily an indicator that a particular target is not responsible for a given phenotype. These proteins were also identified using yeast-two hybrid studies with baits having known disease associations.

The identified components of the ubiquitin ligation cascade therefore represent a drug target for compounds that suppress or activate the cell cycle cells, or cause cell cycle arrest, cause release from cell cycle arrest, inhibit or activate cellular proliferation, activate or inhibit apoptosis, increase sensitivity to chemotherapeutic (adjuvant) reagents, and decrease toxicity of chemotherapeutic reagents. Agents identified in these assays, including small organic molecules, peptides, cyclic peptides, nucleic acids, antibodies, antisense nucleic acids, RNAi, and ribozymes, that modulate cell cycle regulation and cellular proliferation, can be used to treat diseases related to cell cycle. In particular, cell cycle modulators are useful for inhibition of cancer and tumor cell growth, as well as noncancerous disease states caused by pathologically proliferating cells. Such modulators can also be used to modulate the sensitivity of cells to chemotherapeutic agents, such as bleomycin and etoposide, and other agents known to those of skill in the art. Such modulators can also be used to decrease toxicity of such chemotherapeutic reagents. Such modulators can also be used to stimulate the cell cycle or to activate apoptosis, e.g., to stimulate the immune system in infections and other diseases and in the inflammatory process.

Such modulators are useful for treating cancers, such as melanoma, breast, ovarian, lung, gastrointestinal and colon, prostate, and leukemia and lymphomas, e.g., multiple myeloma. In addition, such modulators are useful for treating noncancerous disease states caused by pathologically proliferating cells such as autoimmune disease, thyroid hyperplasia (Grave's disease), psoriasis, benign prostatic hypertrophy, neurofibromas, atherosclerosis, restenosis, and other vasoproliferative disease.

DEFINITIONS

"Ubiquitin ligation pathway or component" refers to ubiquitin and ubiquitin-like molecules (see FIG. 4), and E1, E2, and E3 proteins and their substrates, which are involved in the ubiquitination process (see, e.g., Weissman, *Nature Reviews* 2:169-178 (2001); see also WO 01/75145)).

By "disorder associated with cellular proliferation or the cell cycle" or "disease associated with cellular proliferation or the cell cycle" herein is meant a disease state which is marked by either an excess or a deficit of cellular proliferation or apoptosis, or improper modulation of the cell cycle, or cell cycle arrest. Such disorders associated with increased cellular proliferation include, but are not limited to, cancer and non-cancerous pathological proliferation.

The terms "ubiquitin ligation cascade component" or a nucleic acid encoding "a ubiquitin ligation cascade component" refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by an nucleic acid that encodes a protein as shown in column 1 of FIG. 1, 2, or 3; (2) bind to antibodies, e.g., polyclonal antibodies, raised against an immunogen comprising an amino acid sequence of a protein as shown in column 1 of FIGS. 1, 2, and 3, and conservatively modified variants thereof; (3) specifically hybridize under stringent hybridization conditions to an anti-sense strand corresponding to a nucleic acid sequence encoding an protein of column 1, FIGS. 1, 2, and 3, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a nucleic acid encoding a protein of column 1, FIGS. 1, 2, and 3. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. A protein of the invention typically has activity in a ubiquitin ligase assay (see, e.g., WO 01/17145).

The phrase "functional effects" in the context of assays for testing compounds that modulate activity of a ubiquitin ligation cascade protein includes the determination of a parameter that is indirectly or directly under the influence of a ubiquitin ligation cascade protein, e.g., a phenotypic or chemical effect, such as the ability to increase or decrease cellular proliferation, apoptosis, or cell cycle arrest; or e.g., a physical effect such as ligand or substrate binding or inhibition of ligand or substrate binding. A functional effect therefore includes ligand binding activity, the ability of cells to proliferate, apoptosis, and enzyme activity. "Functional effects" include in vitro, in vivo, and ex vivo activities.

By "determining the functional effect" is meant assaying for a compound that increases or decreases a parameter that is indirectly or directly under the influence of a ubiquitin ligation cascade protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g. binding to antibodies; measuring changes in ligand or substrate binding activity; measuring cellular proliferation; measuring apoptosis; measuring cell surface marker expression; measurement of changes in protein levels for ubiquitin ligation cascade-associated sequences; measurement of RNA stability; phosphorylation or dephosphorylation; ligase activity; identification of downstream or reporter gene expression (CAT, luciferase, β-gal, GFP and the like), e.g., via chemiluminescence, fluorescence, colorimetric reactions, antibody binding, and inducible markers. In one embodiment, the function effect is determined using an in vitro ubiquitin ligase assay or a ubiquitin conjugation assay as described in Examples 2 and 3 of WO 01/17145, using recombinant ubiquitin and ubiquitin-like molecules, E1, E2, and E3 molecules of choice, e.g., those listed in FIGS. 1-4. In another embodiment, the functional effect is determined by assaying for cell cycle modulation using a cell tracker assay and FACS analysis, BRDU staining and FACS analysis, or other assay, as described herein.

"Inhibitors", "activators", and "modulators" of ubiquitin ligation cascade polynucleotide and polypeptide sequences are used to refer to activating, inhibitory, or modulating molecules identified using in vitro and in vivo assays of ubiquitin ligation cascade polynucleotide and polypeptide sequences. Inhibitors are compounds that, e.g., bind to, partially or totally block activity, decrease, prevent, delay activation, inactivate, desensitize, or down regulate the activity or expression of ubiquitin ligation cascade proteins, e.g., antagonists. "Activators" are compounds that increase, open, activate, facilitate, enhance activation, sensitize, agonize, or up regulate ubiquitin ligation cascade protein activity, e.g., agonists. Inhibitors, activators, or modulators also include genetically modified versions of ubiquitin ligation cascade proteins, e.g., versions with altered activity, as well as naturally occurring and synthetic ligands, substrates, antagonists, agonists, antibodies, peptides, cyclic peptides, nucleic acids, antisense molecules, ribozymes, small chemical molecules and the like. Such assays for inhibitors and activators include, e.g., expressing ubiquitin ligation cascade protein in vitro, in cells, or cell membranes, applying putative modulator compounds, and then determining the functional effects on activity, as described above.

Samples or assays comprising ubiquitin ligation cascade proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of ubiquitin ligation cascade proteins is achieved when the activity value relative to the control is about 80%, preferably 50%, more preferably 25-0%. Activation of ubiquitin ligation cascade proteins is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

An "siRNA" molecule or an "RNAi molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety.

An siRNA molecule or RNAi molecule is "specific" for a target nucleic acid if it reduces expression of the nucleic acid by at least about 10% when the siRNA or RNAi is expressed in a cell that expresses the target nucleic acid.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence or amino acid sequence of FIGS. 1-3), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains (RING, ligase), extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., a ligase or RING domain. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda.

Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a ubiquitin ligation cascade protein, polymorphic variants, alleles, orthologs, and conservatively modified variants, or splice variants, or portions thereof, can be selected to obtain only those polyclonal antibodies that are specifically immunoreactive with ubiquitin ligation cascade proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

Assays for Proteins that Modulate the Cell Cycle

High throughput functional genomics assays can be used to identify modulators of the cell cycle. Such assays can monitor changes in cell surface marker expression, proliferation and differentiation, and apoptosis, using either cell lines or primary cells. Typically, the cells are contacted with a cDNA library, an siRNA library, small molecules, antisense molecules, or a random peptide library (encoded by nucleic acids). In one embodiment, the peptides are cyclic or circular. The cDNA library can comprise sense, antisense, full length, and truncated cDNAs. The peptide library is encoded by nucleic acids. The effect of the cDNA, siRNA, or peptide library on the cell cycle is then monitored, using an assay as described above. The effect of the cDNA, siRNA, or peptide can be validated and distinguished from somatic mutations, using, e.g., regulatable expression of the nucleic acid such as expression from a tetracycline promoter. cDNAs, siRNA and nucleic acids encoding peptides can be rescued using techniques known to those of skill in the art, e.g., using a sequence tag. Specific siRNA, cDNA, and peptide sequences can further be used for validation of specific target molecules.

Proteins interacting with the peptide or with the protein encoded by the cDNA can be isolated using a yeast two-hybrid system, mammalian two hybrid system, immunoprecipitation or affinity chromatography of complexed proteins followed by mass spectrometry, or phage display screen, etc. Association with a particular bait provides a disease association for the ubiquitin ligation cascade component. Association of a ubiquitin ligation cascade component with a specific bait indicates that the component is involved in ubiquitination of the bait. Targets so identified can be further used as bait in these assays to identify additional members of the cell cycle pathway, which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667, 973, 5,468,614, 5,525,490, and 5,637,463).

Suitable cell lines include A549, HeLa, Colo205, H1299, MCF7, MDA-MB-231, PC3, HUVEC, HMEC, PrEC, Jurkat, BJAB, HCT116, and cultured mast cells. Cell surface markers can be assayed using fluorescently labeled antibodies and FACS. Cell proliferation can be measured using $^3$H-thymidine incorporation, cell count by dye inclusion, MTT assay, BrdU incorporation, Cell Tracker assay. Apoptosis can be measured using vital dye inclusion, or by assaying for DNA laddering, increases in intracellular calcium, or caspase activation. Growth factor production can be measured using an immunoassay such as ELISA.

cDNA libraries are made from any suitable source. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors.

Isolation of Nucleic Acids Encoding Ubiquitin Ligation Cascade Components

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Ubiquitin ligation cascade nucleic acids, polymorphic variants, orthologs, and alleles that are substantially identical to an amino acid sequence encoded by nucleic acids of FIGS. 1-3 can be isolated using nucleic acid probes and oligonucleotides under stringent hybridization conditions, by screening libraries. Alternatively, expression libraries can be used to clone the ubiquitin ligation cascade protein, polymorphic variants, orthologs, and alleles by detecting expressed homologs immunologically with antisera or purified antibodies made against human ubiquitin ligation cascade proteins or portions thereof.

To make a cDNA library, one should choose a source that is rich in the RNA of choice. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA*, 72:3961-3965 (1975).

A preferred method of isolating ubiquitin ligation cascade nucleic acids and orthologs, alleles, mutants, polymorphic variants, splice variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR and RT-PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of ubiquitin ligation cascade component encoding mRNA in physiological samples, for nucleic acid sequencing, or for other purposes. Genes amplified by the PCR reaction can be purified from agarose gels and cloned into an appropriate vector.

Gene expression of ubiquitin ligation cascade components can also be analyzed by techniques known in the art, e.g., reverse transcription and amplification of mRNA, isolation of total RNA or poly A+ RNA, northern blotting, dot blotting, in situ hybridization, RNase protection, high density polynucleotide array technology, e.g., and the like.

Nucleic acids encoding ubiquitin ligation cascade proteins can be used with high density oligonucleotide array technology (e.g., GeneChip™) to identify ubiquitin ligation cascade proteins, orthologs, alleles, conservatively modified variants, and polymorphic variants in this invention. In the case where the homologs being identified are linked to modulation of the cell cycle, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene of choice is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding ubiquitin ligation cascade proteins, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli*, Bacillus sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.*

132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing ubiquitin ligation cascade components.

After the expression vector is introduced into the cells, the transfected cells are cultured under conditions favoring expression of the protein of choice, which is recovered from the culture using standard techniques identified below.

Purification of Polypeptides

Either naturally occurring or recombinant ubiquitin ligation cascade components can be purified for use in functional assays. Naturally occurring protein can be purified, e.g., from human tissue. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes, *Protein Purification. Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

A. Purification of Protein from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni—NTA agarose resin.

Alternatively, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein can also be separated from other proteins on the basis of its size, net surface charge, hydrophobicity, and affinity for ligands or substrates. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of Ubiquitin Ligation Cascade Protein

A. Assays

Modulation of a ubiquitin ligation cascade protein, and corresponding modulation of the cell cycle, e.g., tumor cell, proliferation, can be assessed using a variety of in vitro and in vivo assays, including cell-based models. Such assays can be used to test for inhibitors and activators of ubiquitin ligation cascade protein, and, consequently, inhibitors and activators of cell cycle, including modulators of chemotherapeutic sensitivity and toxicity. Such modulators of ubiquitin ligation cascade protein are useful for treating disorders related to pathological cell proliferation, e.g., cancer. Modulators of ubiquitin ligation cascade protein are tested using either recombinant or naturally occurring protein of choice, preferably human ubiquitin ligation cascade protein.

Preferably, the ubiquitin ligation cascade protein will have the sequence as encoded by a sequence as shown in FIGS. 1-3 or a conservatively modified variant thereof. Alternatively, the ubiquitin ligation cascade protein of the assay will be derived from a eukaryote and include an amino acid subsequence having substantial amino acid sequence identity to a sequence as shown in FIGS. 1-3. Generally, the amino acid sequence identity will be at least 60%, preferably at least 65%, 70%, 75%, 80%, 85%, or 90%, most preferably at least 95%.

Measurement of cellular proliferation modulation with ubiquitin ligation cascade protein or a cell expressing ubiquitin ligation cascade protein, either recombinant or naturally occurring, can be performed using a variety of assays, in vitro, in vivo, and ex vivo, as described herein. A suitable physical, chemical or phenotypic change that affects activity, e.g., enzymatic activity such as ligase activity, cell surface marker expression, cell proliferation, cell cycle perturbation or arrest, or ligand or substrate binding can be used to assess the influence of a test compound on the polypeptide of this invention. When the functional effects are determined using intact cells or animals, one can also measure a variety of effects, such as, ligand binding, ligase activity, transcriptional changes to both known and uncharacterized genetic markers (e.g., northern blots), changes in cell metabolism, changes related to cellular proliferation, cell surface marker expression, DNA synthesis, marker and dye dilution assays (e.g., GFP and cell tracker assays), contact inhibition, tumor growth in nude mice, etc.

In Vitro Assays

Assays to identify compounds with ubiquitin ligation cascade protein modulating activity can be performed in vitro. Such assays can used full length ubiquitin ligation cascade protein or a variant thereof, or a mutant thereof, or a fragment thereof, such as a RING domain. Purified recombinant or naturally occurring protein can be used in the in vitro methods of the invention. In addition to purified ubiquitin ligation cascade protein, the recombinant or naturally occurring protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In a preferred assay, a ubiquitin conjugation or ligase assay is performed as described in WO 01/75145 (incorporated by referenced in its entirety), Examples 2 and 3, using a recombinant E1, E2, or E3 of choice, as listed in FIGS. 1-3, as well as complementary members of the ubiquitin ligation cascade (see also U.S. Ser. No. 09/542,497, U.S. Ser. No. 09/826,312, and U.S. Ser. No. 10/108,767, herein incorporated by reference in their entirety). A substrate is optional.

In one embodiment, a high throughput binding assay is performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, and ubiquitin ligation cascade component ligand or substrate analogs. A wide variety of assays can be used to identify ubiquitin ligation cascade component-modulator binding, including labeled protein-protein binding assays, electrophoretic mobility shifts (e.g., measuring ubiquitination of a substrate), immunoassays, enzymatic assays such as ligase assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the ubiquitin ligation cascade component protein is washed, interference with binding, either of the potential modulator or of the known ligand or substrate, is determined. Often, either the potential modulator or the known ligand or substrate is labeled.

Cell-Based In Vivo Assays

In another embodiment, the ubiquitin ligation cascade protein is expressed in a cell, and functional, e.g., physical and chemical or phenotypic, changes are assayed to identify modulators of the cell cycle. Cells expressing ubiquitin ligation cascade proteins can also be used in enzymatic assays. Any suitable functional effect can be measured, as described herein. For example, cellular morphology (e.g., cell volume, nuclear volume, cell perimeter, nuclear perimeter, DNA replication), ligand binding, ligase activity, apoptosis, cell surface marker expression, cellular proliferation, GFP positivity and dye dilution assays (e.g., cell tracker assays with dyes that bind to cell membranes), DNA synthesis or content assays (e.g., $^3$H-thymidine and fluorescent DNA-binding dyes such as DAPI, BrdU or Hoescht dye with FACS analysis), are all suitable assays to identify potential modulators using a cell based system. Suitable cells for such cell based assays include both primary cancer or tumor cells and cell lines, as described herein, e.g., A549 (lung), MCF7 (breast, p53 wild-type), H1299 (lung, p53 null), Hela (cervical), PC3 (prostate, p53 mutant), MDA-MB-231 (breast, p53 wild-type), Jurkat (T cell), BJAB (B cell), HUVEC, HMEC, RAMOS, LanCap, and HCT116. Cancer cell lines can be p53 mutant, p53 null, or express wild type p53. The ubiquitin ligation cascade protein can be naturally occurring or recombinant. Also, fragments of the ubiquitin ligation cascade protein or chimeric proteins can be used in cell based assays. In addition, point mutants in the catalytic site or in essential residues required by the catalytic site can be used in these assays.

Cellular ubiquitin ligation cascade polypeptide levels can be determined by measuring the level of protein or mRNA. The level of protein or proteins related to the ubiquitin ligation cascade protein is measured using immunoassays such as western blotting, ELISA and the like with an antibody that selectively binds to the ubiquitin ligation cascade polypeptide or a fragment thereof. For measurement of mRNA, amplification, e.g., using multiplex RT-PCR, PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, regulation of ubiquitin ligation cascade protein expression can be measured using a reporter gene system. Such a system can be devised using a promoter operably linked to a reporter gene such as chloramphenicol acetyltransferase, firefly luciferase, bacterial luciferase, β-galactosidase and alkaline phosphatase. In one embodiment, the ubiquitin substrate level is measured using the reporter. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

Animal Models

Animal models of cellular proliferation also find use in screening for modulators of cellular proliferation. Similarly, transgenic animal technology including gene knockout technology, for example as a result of homologous recombination with an appropriate gene targeting vector, or gene overexpression, will result in the absence or increased expression of the ubiquitin ligation cascade protein. The same technology can also be applied to make knock-out cells. When desired, tissue-specific expression or knockout of the ubiquitin ligation cascade protein may be necessary. Transgenic animals generated by such methods find use as animal models of cellular proliferation and are additionally useful in screening for modulators of cellular proliferation.

Knock-out cells and transgenic mice can be made by insertion of a marker gene or other heterologous gene into an endogenous ubiquitin ligation cascade gene site in the mouse genome via homologous recombination. Such mice can also be made by substituting an endogenous ubiquitin ligation cascade protein with a mutated version of the gene, or by mutating an endogenous ubiquitin ligation cascade protein, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

Exemplary Cell Cycle Assays

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Soft agar growth or colony formation in suspension assays can be used to identify cell cycle modulators. Typically, transformed host cells (e.g., cells that grow on soft agar) are used in this assay. For example, RKO or HCT116 cell lines can be used. Techniques for soft agar growth or colony formation in suspension assays are described in Freshney, *Culture of Animal Cells a Manual of Basic Technique*, $3^{rd}$ ed., Wiley-Liss, New York (1994), herein incorporated by reference. See also, the methods section of Garkavtsev et al. (1996), supra, herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with [$^3$H]-thymidine at saturation density can be used to measure density limitation of growth. See Freshney (1994), supra. The transformed cells, when contacted with cellular proliferation modulators, regenerate a normal phenotype and become contact inhibited and would grow to a lower density.

Contact inhibition and density limitation of growth assays can be used to identify cell cycle modulators which are capable of inhibiting abnormal proliferation and transformation in host cells. Typically, transformed host cells (e.g., cells that are not contact inhibited) are used in this assay. For example, RKO or HCT116 cell lines can be used. In this assay, labeling index with [$^3$H]-thymidine at saturation density is a preferred method of measuring density limitation of growth. Transformed host cells are contacted with a potential modulator and are grown for 24 hours at saturation density in non-limiting medium conditions. The percentage of cells labeling with [$^3$H]-thymidine is determined autoradiographically. See, Freshney (1994), supra. The host cells contacted with the modulator would give arise to a lower labeling index compared to control (e.g., transformed host cells transfected with a vector lacking an insert).

Growth Factor or Serum Dependence

Growth factor or serum dependence can be used as an assay to identify cell cycle modulators. Transformed cells have a lower serum dependence than their normal counterparts (see, e.g., Temin, *J. Natl. Cancer Insti.* 37:167-175 (1966); Eagle et al., *J. Exp. Med.* 131:836-879 (1970)); Freshney, supra. This is in part due to release of various growth factors by the transformed cells. When transformed cells are contacted with the modulator, the cells would reacquire serum dependence and would release growth factors at a lower level.

Tumor Specific Markers Levels

Tumor cells release an increased amount of certain factors (hereinafter "tumor specific markers") than their normal counterparts. For example, plasminogen activator (PA) is released from human glioma at a higher level than from normal brain cells (see, e.g., Gullino, *Angiogenesis, tumor vascularization, and potential interference with tumor growth*. In Mihich (ed.): "Biological Responses in Cancer." New York, Academic Press, pp. 178-184 (1985)). Similarly, tumor angiogenesis factor (TAF) is released at a higher level in tumor cells than their normal counterparts. See, e.g., Folkman, Angiogenesis and cancer, *Sem Cancer Biol*. (1992)).

Tumor specific markers can be assayed to identify modulators which decrease the level of release of these markers from host cells. Typically, transformed or tumorigenic host cells are used. Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); Whur et al., *Br. J. Cancer* 42:305-312 (1980); Gulino, *Angiogenesis, tumor vascularization, and potential interference with tumor growth*. In Mihich, E. (ed): "Biological Responses in Cancer." New York, Plenum (1985); Freshney *Anticancer Res*. 5:111-130 (1985).

Invasiveness into Matrigel

The degree of invasiveness into Matrigel or some other extracellular matrix constituent can be used as an assay to identify cell cycle modulators which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used as host cells. Therefore, cell cycle modulators can be identified by measuring changes in the level of invasiveness between the host cells before and after the introduction of potential modulators. If a compound modulates a ubiquitin ligation cascade protein, its expression in tumorigenic host cells would affect invasiveness.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Apoptosis Analysis

Apoptosis analysis can be used as an assay to identify ubiquitin ligation cascade modulators. In this assay, cell lines, such as RKO or HCT116, can be used to screen cell cycle modulators. Cells are contacted with a putative modulator. The cells can be co-transfected with a construct comprising a marker gene, such as a gene that encodes green fluorescent protein, or a cell tracker dye, or BRDU. The apoptotic change can be determined using methods known in the art, such as DAPI staining and TUNEL assay using fluorescent microscope. For TUNEL assay, commercially available kit can be used (e.g., Fluorescein FragEL DNA Fragmentation Detection Kit (Oncogene Research Products, Cat.#QIA39)+Tetramethyl-rhodamine-5-dUTP (Roche, Cat. #1534 378)). Cells contacted with modulators would exhibit, e.g., an increased apoptosis compared to control.

Cell Cycle Arrest Analysis

Cell cycle arrest can be used as an assay to identify ubiquitin ligation cascade modulators. Any phase of the cell cycle can be measured in this assay, e.g., $G_1$, S, $G_2$, and M, also the $G_0$ state, as well as apoptosis. In this assay, cell lines, such as A549, HeLa, HUVEC, HMEC, prostate cells, RKO or HCT116, can be used to screen ubiquitin ligation cascade modulators. The cells can be co-transfected with a construct comprising a marker gene, such as a gene that encodes green fluorescent protein, or the cells can be contacted with a dye such as a cell tracker dye or BRDU. Methods known in the art can be used to measure the degree of cell cycle arrest. For example, a propidium iodide signal or other dye can be used as a measure for DNA content or synthesis to determine cell cycle profiles on a flow cytometer using FACS. The percent of the cells in each cell cycle can be calculated. Cells contacted with a ubiquitin ligation cascade modulator would exhibit, e.g., a higher number of cells that are arrested in the selected cell cycle phase ($G_1$, S, $G_2$, and M, also the $G_0$ state) compared to control phases of the cell cycle.

Tumor Growth In Vivo

Effects of ubiquitin ligation cascade modulators on cell growth can be tested in transgenic or immune-suppressed mice. Knock-out transgenic mice can be made, in which the endogenous ubiquitin ligation cascade gene is disrupted. Such knock-out mice can be used to study effects of the ubiquitin ligation cascade component, e.g., as a cancer model, as a means of assaying in vivo for compounds that modulate a ubiquitin ligation cascade component, and to test the effects of restoring a wild-type or mutant ubiquitin ligation cascade component to a knock-out mice.

Knock-out cells and transgenic mice can be made by insertion of a marker gene or other heterologous gene into the endogenous gene site in the mouse genome via homologous recombination. Such mice can also be made by substituting the endogenous gene with a mutated version of the gene, or by mutating the endogenous gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987). These knock-out mice can be used as hosts to test the effects of various modulators on cell growth.

Alternatively, various immune-suppressed or immune-deficient host animals can be used. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. Hosts are treated with modulators, e.g., by injection. After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, modulators which are capable, e.g., of inhibiting abnormal cell proliferation can be identified.

B. Modulators

The compounds tested as modulators of ubiquitin ligation cascade protein can be any small organic molecule, or a biological entity, such as a protein, e.g., an antibody or peptide, a sugar, a nucleic acid, e.g., an antisense oligonucleotide or a ribozyme or RNAi, or a lipid. Alternatively, modulators can be genetically altered versions of a ubiquitin ligation cascade protein. Typically, test compounds will be small organic molecules, peptides, circular peptides, RNAi, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a ubiquitin ligation cascade protein, or a cell or tissue expressing an ubiquitin ligation cascade protein, either naturally occurring or recombinant. In another embodiment, the invention provides solid phase based in vitro assays in a high throughput format, where the ubiquitin ligation cascade protein or ubiquitin ligation cascade substrate is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for ubiquitin ligation cascade proteins in vitro, or for cell-based or membrane-based assays comprising a ubiquitin ligation cascade protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of Polypeptides

In addition to the detection of a ubiquitin ligation cascade gene and gene expression using nucleic acid hybridization technology, one can also use immunoassays to detect ubiquitin ligation cascade proteins of the invention. Such assays are useful for screening for modulators of ubiquitin ligation cascade proteins, as well as for therapeutic and diagnostic applications. Immunoassays can be used to qualitatively or quantitatively analyze ubiquitin ligation cascade protein. A general overview of the applicable technology can be found in Harlow & Lane, *Antibodies: A Laboratory Manual* (1988).

A. Production of Antibodies

Methods of producing polyclonal and monoclonal antibodies that react specifically with ubiquitin ligation cascade proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256: 495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of a ubiquitin ligation cascade protein may be used to produce antibodies specifically reactive with the ubiquitin ligation cascade protein. For example, a recombinant ubiquitin ligation cascade protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-ubiquitin ligation cascade proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular ubiquitin ligation cascade protein ortholog, such as a human ortholog, can also be made, by subtracting out other cross-reacting orthologs from a species such as a non-human mammal. In this manner, antibodies that bind only to the protein of choice may be obtained.

Once the specific antibodies against a ubiquitin ligation cascade protein are available, the protein can be detected by a variety of immunoassay methods. In addition, the antibody can be used therapeutically as a ubiquitin ligation cascade protein modulators. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

Protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the ubiquitin ligation cascade protein or antigenic subsequence thereof). The antibody (e.g., anti-ubiquitin ligation cascade protein) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled ubiquitin ligation cascade protein or a labeled anti-ubiquitin ligation cascade protein antibody. Alternatively, the labeling agent may be a third moiety, such a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111: 1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting ubiquitin ligation cascade protein in samples may be either competitive or noncompetitive. Noncompetitive immunoassays are assays in which the amount of antigen is directly measured. In one preferred "sandwich" assay, for example, the anti-ubiquitin ligation cascade protein antibodies can be bound directly to a solid substrate on which they are immobilized. These immobilized antibodies then capture the ubiquitin ligation cascade protein present in the test sample. Proteins thus immobilized are then bound by a labeling agent, such as a second ubiquitin ligation cascade protein antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of ubiquitin ligation cascade protein present in the sample is measured indirectly by measuring the amount of a known, added (exogenous) ubiquitin ligation cascade protein displaced (competed away) from an anti-ubiquitin ligation cascade protein antibody by the unknown ubiquitin ligation cascade protein present in a sample. In one competitive assay, a known amount of ubiquitin ligation cascade protein is added to a sample and the sample is then contacted with an antibody that specifically binds to ubiquitin ligation cascade protein. The amount of exogenous ubiquitin ligation cascade protein bound to the antibody is inversely proportional to the concentration of ubiquitin ligation cascade protein present in the sample. In a particularly preferred embodiment, the antibody is immobilized on a solid substrate. The amount of ubiquitin ligation cascade protein bound to the antibody may be determined either by measuring the amount of ubiquitin ligation cascade protein present in ubiquitin ligation cascade protein/antibody complex, or alternatively by measuring the amount of remaining uncomplexed protein. The amount of ubiquitin ligation cascade protein may be detected by providing a labeled ubiquitin ligation cascade molecule.

A hapten inhibition assay is another preferred competitive assay. In this assay the known ubiquitin ligation cascade protein is immobilized on a solid substrate. A known amount of anti-ubiquitin ligation cascade protein antibody is added to the sample, and the sample is then contacted with the immobilized ubiquitin ligation cascade protein. The amount of anti-ubiquitin ligation cascade protein antibody bound to the known immobilized ubiquitin ligation cascade protein is inversely proportional to the amount of ubiquitin ligation cascade protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a ubiquitin ligation cascade protein can be immobilized to a solid support. Proteins are added to the assay that compete for binding of the antisera to the immobilized antigen. The ability of the added proteins to compete for binding of the antisera to the immobilized protein is compared to the ability of the ubiquitin ligation cascade protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a ubiquitin ligation cascade protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the ubiquitin ligation cascade protein that is required to inhibit 50% of binding, then the second protein is said to specifically bind to the polyclonal antibodies generated to ubiquitin ligation cascade immunogen.

Other Assay Formats

Western blot (immunoblot) analysis is used to detect and quantify the presence of ubiquitin ligation cascade protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the ubiquitin ligation cascade protein. The anti-ubiquitin ligation cascade protein antibodies specifically bind to the ubiquitin ligation cascade protein on the solid support. These antibodies may be directly labeled or alternatively may be subsequently detected using labeled antibodies (e.g., labeled sheep anti-mouse antibodies) that specifically bind to the anti-ubiquitin ligation cascade protein antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize ubiquitin ligation cascade protein, or secondary antibodies that recognize anti-ubiquitin ligation cascade protein.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cellular Transfection and Gene Therapy

The present invention provides the nucleic acids of ubiquitin ligation cascade protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a ubiquitin ligation cascade protein of the present invention, thereby mitigating the effects of absent, partial inactivation, or abnormal expression of a ubiquitin ligation cascade gene, particularly as it relates to cellular proliferation. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Yeast Two-Hybrid Assays

Members of the ubiquitin ligation cascade identified herein were isolated in a yeast two-hybrid screen baited with known proteins such as FRIP/DOK2, a ras GAP binding adaptor protein that plays a role in IL-4 and EGF receptor signaling; MYT1, which is a Wee1 family member that regulates cdc2 and G-S transitions during cell cycle progression; and XIAP, which is an IAP family member that inhibits pro-apoptotic caspase pathways (for other baits, see FIG. 1, column 6, and FIG. 2, column 7. UBcH6 and FLJ25157 bound to FRIP, MMS, UEV1, and CDC34 bound to Myt1, and Ubc13 bound to XIAP (for other baits and hits, see FIG. 1, column 1 and FIG. 2, column 1). Proteins interacting with the bait peptide are isolated using yeast two-hybrid systems or mammalian two hybrid systems known to those of skill in the art (see, e.g., Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 9578 (1991); and U.S. Pat. Nos. 5,283,173, 5,667,973, 5,468,614, 5,525,490, and 5,637,463).

Example 2

Selection of siRNA Target Sites for Phenotype Assays siRNA was used to inhibit selected target molecules, whose function was then examined in phenotype assays, e.g., cell cycle assays.

Begin with the AUG start codon of the mRNA to be targeted, skip the first 75 bases and scan downstream for AA dinucleotide sequences. Record the occurrence of each AA and the 3' adjacent 19 nucleotides as potential siRNA target sites (the two base pair sequences 3' to the 19 mer do not seem to matter). There is no indication that a longer siRNA will do better than the current 21 mer used herein, however, longer siRNA molecules can be designed.

Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with binding of the siRNA endonuclease complex.

Check each potential target sites and make sure its GC content is between 30-70% and it does not have a stretch of more than 4 Gs or Cs.

Check each potential target sites (using BLAST search for human genes) and make sure it does not sit on an intron/exon boundary.

Check and make sure each potential target site does not contain a SNP.

Compare the potential target sites to the appropriate database and eliminate from consideration any target sequences with significant homology (with a stretch of bases >=16 nucleotides or so identical) to other coding sequences.

Select 3 to 4 target sequences along the length of the gene to evaluate whether the 5', 3', or medial portions of mRNAs are more susceptible to siRNA induced degradation.

Example 3

Cell Cycle Analysis Using BRDU Staining and FACS Analysis

Transfection of siRNA duplexes: Cells (A549, Hela) were plated 24 hours before transfection on 24-will plate (Costar) in 500 µl growth media supplemented with 10% FBS. siRNA were obtained from Dharmacon Inc. or Xeragon. Inc.

60 pmol of siRNA duplex was mixed with 50 µl of Opti-Mem media (Gibco). In another tube 3 µl of Oligofectamine Reagent (Invitrogen) was mixed with 12 µl of Opti-Mem media and incubated 10 min at room temperature. Solutions were combined and incubated 25 min at room temperature. Then 32 µl of fresh of Opti-Mem media was added to final volume of 100 µl. The 100 µl of siRNA-Oligofectamine mix was added to the cells. 16 hours after transfection cells were washed 2 times with PBS, trypsinized and plated on 6 well plate with density 2500 cells/cm2 for Cell Cycle analysis with BrdU and FACScan instrument or 1500 cells per well onto 96 well tissue culture plate (Costar) for assay with Cellomics instrument.

Cell Cycle analysis with BrdU: 72 hours after transfection BrdU was added at concentration 10µ. 4 hours after incubation with BrdU cells were collected, fixed and prepared for Cell Cycle analysis as previously described (see, e.g., Kastan et al., Cancer Research 51:6304-6311 (1991); White et al., Genes and Development 8:666-677 (1994); Serrano et al, Cell 88(5):593-602 (1997)). Cell cycle analysis was performed using a Becton Dickinson FACScan instrument.

Example 4

Cell Cycle Analysis Using Cell Tracker Dye Assays and FACS Analysis siRNA, cDNA, or peptide-encoding nucleic acids are used to transfect cells (e.g., cDNA dominant negative mutants or effectors, or trans dominant effectors (peptides, siRNA, antisense, etc.), or inhibitors or activators). cDNA and peptide-encoding nucleic peptide libraries may be used. In one embodiment, the peptide libraries are randomized. cDNA and siRNA may be targeted to a specific gene or transcript for functional knockout studies.

Transfected cells were stained with cell tracker dyes to monitor the cell cycle. Cells with brighter staining were identified as cell cycle-altered or -arrested cells, e.g., using FACS analysis (see, e.g., U.S. Ser. No. 09/157,748). Cycling cells can be eliminated by transfection with a retrovirus encoding the diphtheria toxin alpha chain. Cycling cells are susceptible to retroviral infection, but cell cycle arrested cells are not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method for identifying a compound that modulates the cell cycle, the method comprising the steps of:
   (i) contacting a polypeptide comprising an E2 polypeptide with an amino acid sequence having at least 90% identity to SEQ ID NO: 2 with the compound, wherein said E2 polypeptide has ubiquitin conjugation enzyme activity;
   (ii) determining the effect of the compound upon the E2 polypeptide in vitro using a ubiquitin ligase assay;
   (iii) selecting a compound that has an effect upon the E2 polypeptide as measured by the ubiquitin ligase assay;
   (iv) determining the effect of the compound selected in (iii) on the cell cycle using a cell cycle assay in a cell comprising the E2 polypeptide; and
   (v) selecting a compound determined in (iv) to have an effect on the cell cycle, thereby identifying a compound that modulates the cell cycle.

2. The method of claim 1, wherein the E2 polypeptide is recombinant.

3. The method of claim 1, wherein the compound is an RNAi molecule.

4. The method of claim 1, wherein the compound is an antibody.

5. The method of claim 1, wherein the compound is an antisense molecule.

6. The method of claim 1, wherein the compound is a small organic molecule.

7. The method of claim 1, wherein the compound is a peptide.

8. The method of claim 7, wherein the peptide is circular.

9. The method of claim 1, wherein the E2 polypeptide comprises an amino acid sequence having at least 95% identity to the full length sequence of SEQ ID NO: 2.

10. The method of claim 1, wherein the cell cycle assay comprises determining the phase of the cell cycle.

11. The method of claim 10, wherein determining the phase of the cell cycle comprises flow cytometric analysis.

12. The method of claim 1, wherein the cell cycle assay comprises one or more of the following: a soft agar growth assay, a colony formation assay, a contact inhibition assay, a density limitation growth assay, a growth factor or serum dependence assay, an apoptosis assay, a cell cycle arrest assay, or a tumor growth assay.

13. A method for identifying a compound that modulates the cell cycle, the method comprising:
   contacting a cell comprising an E2 polypeptide with an amino acid sequence having at least 90% identity to SEQ ID NO: 2 with the compound, wherein the E2 polypeptide has ubiquitin conjugation enzyme activity; and
   determining the effect of the compound upon the cell cycle using a cell cycle assay comprising:
      application of fluorescent dye or BRDU to the cell, and
      fluorescence activated cell sorting (FACS) analysis of the cells to determine the phase of the cell cycle, thereby identifying a compound that modulates the cell cycle.

* * * * *